United States Patent [19]

Midler, Jr. et al.

[11] 4,073,743

[45] Feb. 14, 1978

[54] PROCESS FOR PREPARING AN EMULSION

[75] Inventors: Michael Midler, Jr., East Brunswick; Edward Paul, Chatam Township, Union County, both of N.J.

[73] Assignee: Merck & Co., Inc., Rahway, N.J.

[21] Appl. No.: 714,428

[22] Filed: Aug. 13, 1976

Related U.S. Application Data

[63] Continuation-in-part of Ser. No. 569,022, April 17, 1975, abandoned.

[51] Int. Cl.² .............................................. B01J 13/00
[52] U.S. Cl. .................................... 252/309; 252/314; 424/85; 424/86; 424/88; 424/89; 424/172
[58] Field of Search ............... 252/309, 314; 424/172, 424/86

[56] References Cited

U.S. PATENT DOCUMENTS

| 2,254,049 | 8/1941 | Schutte | 252/314 |
|---|---|---|---|
| 2,322,822 | 6/1943 | Brown | 252/309 X |
| 2,744,870 | 5/1956 | Stillebroer et al. | 252/309 X |
| 2,948,686 | 8/1960 | Gianladis | 252/309 X |
| 3,100,178 | 8/1963 | McLean, Jr. et al. | 424/172 X |
| 3,399,263 | 8/1968 | Strazdins et al. | 424/86 X |
| 3,663,235 | 5/1972 | Menz et al. | 252/309 X |

*Primary Examiner*—Richard D. Lovering
*Attorney, Agent, or Firm*—Donald J. Perrella

[57] ABSTRACT

A process for preparing a highly stable water-in-oil type emulsion consisting of (a) a disperse aqueous phase; (b) a continuous oil phase containing isomannide monooleate emulsifier and a non-hydrated physiologically acceptable fatty acid metal salt. A particular use of the invention is the preparation of an emulsion adjuvant vaccine, wherein the vaccine is incorporated in the aqueous phase.

The emulsion is prepared by mixing the aqueous and oil phases at a relatively low agitator speed, optionally cooling, increasing the speed of agitation to form an emulsion and optionally homogenizing the emulsion.

12 Claims, No Drawings

PROCESS FOR PREPARING AN EMULSION

RELATED APPLICATION

The subject application is a continuation-in-part of copending application Ser. No. 569,022, filed April 17, 1975 and now abandoned.

DETAILED DESCRIPTION

The specific difficulty overcome by the process of this invention is that of preparing an emulsion of extremely uniform composition with the required stability to resist separation 1) when stored at 37° C. for 30 days in a static condition and 2) when transferred through process lines as required for processing and syringe filling. A secondary difficulty likewise overcome is complete (>90%) removal of the premix emulsion out of the mixing vessel. The fundamental principle employed in the process of the present invention is the preparation of a water-in-oil emulsion of a fixed composition with the proper mixing and polishing operations to give the required aqueous phase drop size and drop size distribution in a suitably prepared oil phase to achieve the required stability. The process of the present invention is described in terms of specifically defined temperature limits, mixing rates, and equipment specifications which produce an emulsion with the required characteristics.

In accordance with the present invention the manufacturer is provided with a novel process for preparing a highly stable emulsion consisting of (a) a disperse aqueous phase; (b) a continuous oil phase containing isomannide monooleate emulsifier and a non-hydrated physiologically acceptable fatty acid metal salt.

Adjuvant emulsions prepared by the novel process of the invention may be employed as carriers for pharmaceutically active drugs or may be used to potentiate the antibody response of antigenic materials. In the latter case, the terms "antigen" and "antigenic material" which are used interchangeably herein include one or more non-viable immunogenic or desensitizing (antiallergic) agents of bacterial, viral or other origin. The antigen component employed in the present process may consist of a dried powder, an aqueous solution, an aqueous suspension and the like, including mixtures of the same, containing a non-viable immunogenic or desensitizing agent or agents. The preferred antigen component employed in the present process is an aqueous influenza virus suspension.

The specific oil employed in the adjuvant composition of the invention is not critical. Any physiologically acceptable injectable oil or mixtures thereof including those oils which satisfy the specifications of the United States Pharmacopeia or National Formulary may be utilized in the practice of the invention. Representative members include peanut oil, safflower oil, soya bean oil, cottonseed oil, mineral oils of a pharmaceutical grade such as light liquid paraffin and light mineral oil, chaulmoogra oil, corn oil, persic oil, olive oil, sesame oil, almond oil, castor oil, squalane, isopropyl myristate and coconut oil. Of particular preference are peanut oil and highly purified light mineral oil.

The metal cation of the fatty acid metal salt employed in the adjuvant may be defined as those metals which are capable of forming a salt with a fatty acid. Typical of metals which are included within this category are aluminum, magnesium, iron, cerium, zinc, copper, lanthanum, bismuth, and manganese among others. The fatty acid component includes those acids derived from a saturated or unsaturated monobasic acid of 12 to 24 carbons, such as lauric, myristic, palmitic, stearic, arachidic, behenic, lignoceric, ricinoleic, oleic, erucic, linoleic and the like.

Representative members of the class of non-hydrated fatty acid metal salts, including mixtures thereof, which may be incorporated in the emulsion include: aluminum laurate, magnesium myristate, cerium palmitate, zinc stearate, copper behenate, lanthanum lignocerate, bismuth oleate, manganese linoleate, aluminum myristate, magnesium palmitate, cerium stearate, zinc arachidate, copper lignocerate, lanthanum ricinoleate, bismuth erucate, manganese laurate, aluminum palmitate, magnesium stearate, cerium arachidate, zinc behenate, copper ricinoleate, iron myristoleic, lanthanum oleate, bismuth linoleate, and manganese behenate. Preferably the fatty acid metal salt is aluminum monostearate.

While the selection of the vegetable oil, of the aqueous phase of the adjuvant composition and of the fatty acid metal salt is not critical, it is critical that the emulsifying agent, isomannide monooleate, be present in the oil phase of the adjuvant emulsion.

The proportion of the oil and the aqueous phases in the emulsion may vary over a wide range, however, an effective adjuvant composition may be achieved utilizing from about 42.5 to about 48% of oil phase, from about 2 to about 7.5% fatty acid metal salt and isomannide monooleate and from about 45 to about 55% of aqueous phase by volume wherein in the selected composition the sum of the components is always 100%. The preferred composition contains about 50% (inclusive of the fatty acid metal salt and isomannide monooleate) by volume of oil phase and about 50% of aqueous phase by volume, wherein the preferred composition of the oil phase is about 89.0% of oil, such as peanut oil, about 6.7% isomannide monooleate and about 4.3% aluminum monostearate by weight. The isomannide monooleate is highly purified, about 80% pure or higher, i.e., about 90% or above. For human vaccines, it is preferred to use C.P. grade (better than 98%).

The adjuvant emulsion prepared by the novel process of this invention finds utility as a vehicle for parenteral administration of chemotherapeutic or immunological substances. It has the advantage of increasing the efficacy of the antigen over that obtainable with aqueous preparations. Another desirable feature is that it is free of extraneous ionic materials as may be present in prior art preparations.

When the adjuvant emulsion prepared by the novel process of this invention, is employed as a vehicle for an immunological substance, the antigen (or antigens) is preferably incorporated in the aqueous phase prior to the addition of the aqueous phase to the oil. The immunological agent advantageously is used in purified or concentrated form. It may be a dried solid, or an adsorbate on a parenterally acceptable adsorbant, for example aluminum phosphate, aluminum hydroxide, pumice or kieselguhr.

The aqueous phase may conveniently be comprised of the antigenic material in a parenterally acceptable liquid. For example, the aqueous phase may be in the form of a vaccine in which the antigen is dissolved in a balanced salt solution, physiological saline solution, phosphate buffered saline solution, tissue culture fluids or other media in which the organism may have been grown. The aqueous phase also may contain preservatives and/or substances conventionally incorporated in vaccine preparations.

The antigen may be in the form of purified or partially purified antigen derived from bacteria, viruses, rickettsia or their products, or extracts of bacteria, viruses, or rickettsia, or the antigen may be an allergen such as pollens, dusts, danders, or extracts of the same or the antigen may be in the form of a poison or a venom derived from poisonous insects or reptiles. In all cases the antigens will be in the form in which their toxic or virulent properties have been reduced or destroyed and which when introduced into a suitable host will either induce active immunity by the production therein of antibodies against the specific microorganisms, extract or products of microorganisms used in the preparation of the antigen or, in the case of allergens, they will aid in alleviating the symptoms of the allergy due to the specific allergen. The antigens can be used either singly or in combination; for example, multiple bacterial antigens, multiple viral antigens, multiple rickettsial antigens, multiple bacterial or viral toxoids, multiple allergens or combinations of any of the foregoing products can be combined in the aqueous phase of the adjuvant composition of this invention. Antigens of particular importance are derived from bacteria such as *H. pertussis, Leptospira pomona* and *icterohaemorrhagiae, S. typhosa, S. paratyphi* A and B, *C. diphtheriae, C. tetani, C. botulinum, C. perfringens, C. feseri* and other gas gangrene bacteria, *B. anthracis, P. pestis, P. multocida, V. cholerae* and the like; from viruses as polio virus (multiple types), adeno virus (multiple types), parainfluenza virus (multiple types), measles, mumps, respiratory syncytial virus, influenza (various types), shipping fever virus ($SF_4$), Western and Eastern equine encephalomyelitis, Japanese B. encephalomyelitis, Russian Spring Summer encephalomyelitis, hog cholera virus, Newcastle disease virus, fowl pox, rabies, feline and canine distemper and the like viruses, from rickettsiae as epidemic and endemic typhus or other members of the spotted fever group, from various spider and snake venoms or any of the known allergens for example from ragweed, house dust, pollen extracts, grass pollens and the like.

The novel process of the present invention of preparing a water-in-oil emulsion of an aqueous vaccine in an oil phase is described by the following steps: (a) mixing the aqueous and oil phases at a relatively low agitator speed, (b) optionally cooling, (c) increasing the speed of agitation to form an emulsion, and (d) optionally homogenizing the emulsion.

The novel process of the present invention is carried out according to the following steps: (a) mixing the aqueous and oil phases wherein the oil phase contains isomannide monooleate and a non-hydrated physiologically acceptable fatty acid metal salt at from about 9° to about 35° C. and preferably at from about 15° to about 17° C. at a relatively low agitator speed, (b) optionally cooling to about 9° to about 12° C., (c) increasing the speed of agitation to form a suitable emulsion and (d) optionally homogenizing this emulsion by any number of known mechanical means, for example by the use of a colloid mill, Waring or other blender, homogenizers, vibrators, pulsators, or other mechanical devices for particle reduction to obtain the required emulsion viscosity, viscosity stability, and resistance to separation during storage or during flow to allow filling into syringes.

The preferred process for producing a homogeneous blend of phases according to step (a) is by mixing the aqueous and oil phases at a temperature range of from about 15° to about 17° C. in a cylindrical vessel containing fluid wherein the ratio of the height of the fluid to the diameter of the vessel is approximately 2, such vessel outfitted with three turbine agitators of diameter 0.3 to 0.5 times the vessel diameter. The type of turbine used is preferably the bar type, but most other types except the pitched blade type are acceptable. The agitator speed employed for the relatively low speed blending is such that it is sufficient to achieve blending of the phases but such that the value of the term $N^3D^5/V$ remains below about $80 \times 10^9$ where N=rpm, D=agitator diameter (inches), and V=volume of emulsion (liters). The premix is formed according to step (b) by cooling the blend to the range of about 9°-12° C. and preferably about 10°-11° C. and according to step (c) by raising the speed of agitation such that the value of the term, $N^3D^5/V$ increases to above about $140 \times 10^9$. The emulsion is then further processed according to step (d) by homogenizing by any number of known mechanical means, preferably in a colloid mill having about 7 to about 17 mil rotor/stator gap width, operating in the range of about 1,500 to about 1,800 rpm at a flow through rate of about 3.0 to about 4.5 liters/minute of the feed premix.

The novel process thus described achieves its objectives as follows: (a) Uniformity of composition is achieved by the pre-mix procedure at about 9° to about 12° C., which results in a pseudo-stable emulsion of uniform blend. (b) Stability at 37° C. in a static condition is achieved by the uniformity of composition and the processing in the premix and homogenizing stages. (c) Stability to passage through transfer lines is achieved by the cooling step in the premix, which permits the product leaving the homogenizer to be cool enough to resist orthokinetic flocculation. (d) Efficient removal of the emulsion from the mixing vessel is achieved by the choice of agitator diameter and speed, which control the viscosity of the premix to a level high enough to be stable until put through the homogenizer, but low enough to flow cleanly out of the mixing vessel.

When the emulsion of the present invention is used as the carrier for an influenza vaccine which is administered at a dosage level of about 0.5 ml., the aqueous and oil phases wherein the oil phase contains isomannide monooleate and a non-hydrated physiologically acceptable metal salt, mixing preferably takes place at a temperature of from about 9° to about 25° C. When the same amount of antigen is administered at a higher dosage level of about 2.0 ml., however, the mixing may take place at temperatures of from about 9° to about 35° C.

The following examples, wherein the aqueous phase comprises aqueous influenza vaccine, are provided for illustrative purposes and may include particular features of the invention; however, the example should not be construed as limiting the invention, variations of which are possible without departing from the spirit or scope thereof.

In the following examples, the abbreviation "CCA" refers to Chick Cell Agglutinin which is determined by the method described in J. Immunology 45:273 (1942), Hirst and Pickles.

EXAMPLE 1

A composition consisting of the following ingredients:

a. 4000 ml. of oil phase at ambient temperature;
 b. 4000 ml. aqueous influenza virus suspension at 5° C.

wherein the oil phase is composed of peanut oil USP 89.5% by weight, isomannide monooleate C.P. 6.8% by weight and aluminum monostearate C.P. 3.7% by weight and the vaccine consists of phosphate-buffered saline containing $A_2$/Aichi 4000 CCA units/0.5 ml. is introduced into a 6 inch diameter cylindrical borosilicate glass vessel equipped with three bar curved blade turbine agitators (manufactured by Mixing Equipment Company, Rochester, N.Y.), 2½ inch diameter, driven by a ½ hp variable speed electric motor in a rotational direction such that the agitator's leading edges cut into the fluid. Both the oil vehicle and cold (5° C.) vaccine are introduced into the vessel at ambient temperature and without agitation.

The process is carried out by mixing the two phases at 500 rpm for approximately 2 minutes, followed by increasing the speed of agitation to 2,590 rpm and holding at this speed for 35 seconds. The final temperature of the emulsion is 12° C. and its apparent viscosity is 127,000 cp (centipoise) (as measured on a Brookfield viscometer, Model LVT on a Helipath stand, 1.5 rpm T-F spindle, manufactured by Brookfield Engineering Laboratories, Inc., Stoughton, Mass.).

The emulsion thus formed has the following desirable characteristics:

a. uniform composition throughout batch (determined by Karl Fisher water determination);

b. apparent viscosity of 127,000 cp, as mentioned above;

c. electrical conductivity 0μ amps;

d. adequate iceberg appearance on water—minimal iridescence or dispersion;

e. negligible unemulsified aqueous phase; and f. the emulsion is stable at 37° C. for at least 30 days.

EXAMPLE 2

A composition consisting of the following ingredients:

a. 2666 ml. of oil phase at 9° C.

b. 2666 ml. aqueous influenza virus suspension at 9° C. wherein the oil phase is composed of peanut oil USP 89.5% by weight, isomannide monooleate C.P. 6.8% by weight and aluminum monostearate C.P. 3.7% by weight and the vaccine consists of phosphate-buffered saline containing $A_2$/Aichi 4000 CCA units/0.5 ml. is introduced into a 6 inch diameter cylindrical borosilicate glass vessel equipped with three turbine agitators (manufactured by Bench Scale Equipment Co., Dayton, Ohio), top and bottom straight bladed and the middle curved blade rotating in the cutting direction, all 2½ inch diameter, driven by a ½ hp variable speed electric motor. Both the oil vehicle and vaccine are introduced into the vessel at ambient temperature and without agitation.

The process is carried out by mixing the two phases at 1,035 rpm for 3 minutes followed by increasing the speed of agitation to 2,590 rpm and holding at this speed for 2 minutes. The temperature of the emulsion is 14° C. and its apparent viscosity is 180,000 cp (centipoise) (as measured on a Brookfield viscometer, Model LVT on a Helipath stand, 1.5 rpm T-F spindle, manufactured by Brookfield Engineering Laboratories, Inc., Stoughton, Mass.).

The emulsion is poured into a chilled pressure feed tank equipped with a piston and a plug valve in the outlet at the bottom of the tank. The entire assembly is mounted on a chilled colloid mill (Gaulin Colloid Mill, Model 2F, Gaulin Manufacturing Co., Everett, Mass.). The motor speed of the colloid mill is 1,725 rpm and the rotor/stator gap is set at 10 mils. The feed is pressurized to 55 lb./sq. in. gauge and the plug valve is opened and the material processed in a single pass through the mill. "Polished" emulsion is expelled at a temperature of 20° C. The homogenized emulsion thus formed has the following desirable characteristics:

a. uniform composition throughout batch (determined by Karl Fisher water determination);

b. apparent viscosity (measured by the method described above) 534,000 cp;

c. electrical conductivity 0μ amps;

d. excellent iceberg appearance on water—no iridescence or dispersion;

e. completely free of any unemulsified aqueous phase; and f. the emulsion is stable at 37° C. for at least 30 days.

EXAMPLE 3

A composition consisting of the following ingredients:

a. 2900 ml. of oil phase ambient temperature;

b. 2900 ml. of aqueous influenza virus suspension at 4° C.

wherein the oil phase is composed of peanut oil USP 89.0% by weight, isomannide monooleate C.P. 6.7% by weight and aluminum monostearate C.P. 4.3% by weight and the vaccine consists of phosphate-buffered saline containing $A_2$/Aichi 4,000 CCA units/0.5 ml. is introduced into a 6 inch diameter cylindrical borosilicate glass vessel equipped with three bar turbine agitators (manufactured by Mixing Equipment Company, Rochester, N.Y.), 2½ inch diameter, driven by a ½ hp variable speed electric motor. Both the oil vehicle and cold (4° C) vaccine are introduced into the vessel at ambient temperature and without agitation.

The process is carried out by mixing the two phases at 300 rpm, wherein the initial net temperature is 14° C., continuing to stir for 3 hours in a cold room (5° C.) during which time the temperature of the mixture is lowered to 10° C., followed by increasing the speed of agitation to 1725 rpm and holding at this speed for 1½ minutes. The speed is then increased to 2070 rpm for 1½ minutes. The final temperature of the emulsion is 13° C. and its apparent viscosity is 107,000 cp (centipoise) (as measured on a Brookfield viscometer, Model LVT on a Helipath stand, 1.5 rpm T-F spindle, manufactured by Brookfield Engineering Laboratories, Inc., Stoughton, Mass.). This apparent viscosity remains unchanged for 1 to 2 hours at 12° to 14° C.

The emulsion thus formed has the following desirable stability characteristics:

a. uniform composition throughout batch (determined by Karl Fisher water determination);

b. apparent viscosity of 107,000 cp, as mentioned above;

c. electrical conductivity 0μ amps;

d. adequate iceberg appearance on water—minimal irridescence or dispersion;

e. negligible unemulsified aqueous phase; and f. the emulsion is stable at 37° for at least 30 days.

EXAMPLE 4

The emulsion produced in Example 3 is "polished" by homogenizing in a colloid mill as follows:

The emulsion is poured into a chilled pressure feed tank equipped with a piston and a plug valve in the outlet at the bottom of the tank. The entire assembly is mounted on a chilled colloid mill (Gaulin Colloid Mill, Model 2F, Gaulin Manufacturing Co., Everett, Mass.). The motor speed of the colloid mill is 1725 rpm and the rotor/stator gap is set at 12.5 mils. The premix feed is pressurized to 55 lb./sq. in. gauge and the plug valve is opened and the material processed in a single pass through the mill. The "polished" emulsion is expelled at a temperature of 19° C. The homogenized emulsion thus formed has the following desirable characteristics:

a. uniform composition throughout batch (determined by Karl Fisher water determination);

b. apparent viscosity (measured by the method described above) 622,000 cp;

c. electrical conductivity $0\mu$ amps;

d. excellent iceberg appearance on water—no iridescence or dispersion;

e. completely free of any unemulsified aqueous phase;

f. the emulsion is stable at 37° C. for at least 30 days; and g. the emulsion prepared can be transferred through about 3 feet of process line as required for syringe filling without release of excessive free aqueous phase in the line (i.e., less than 3%). A suitable dose of influenza vaccine for immunizing humans can be prepared by filling syringes with 0.5 ml. of the emulsion. A 0.5 ml. dose contains 1,000 CCA units of vaccine.

While the invention has been illustrated by specific examples which describe the preparation of representative compositions comprising antigen incorporated in the aqueous phase of adjuvant vehicles, it is to be understood that modifications and variations can be made in selecting the ingredients and process conditions in the practice of this invention within the framework of the disclosure and of the appended claims.

What is claimed is:

1. The method of preparing a water-in-oil emulsion, wherein the oil phase contains isomannide monooleate and a non-hydrated physiologically acceptable fatty acid metal salt, which comprises:

mixing the aqueous and oil phases at about 9° to about 35° C. at a relatively low agitator speed such that the value of the term $N^3D^5/V$ remains below about $80 \times 10^9$ wherein N = rpm, D = agitator diameter (inches), V = emulsion volume (liters); and increasing the agitator speed such that the value of the term $N^3D^5/V$ wherein N, D, and V are as defined above, is above about $140 \times 10^9$ to form a stable emulsion.

2. The method of claim 1 additionally including the step of cooling the aqueous and oil phases that have been mixed at relatively low agitator speed to from about 9° to about 12° C.

3. The method of claim 1 additionally including the step of homogenizing the stable emulsion.

4. The method of claim 1 wherein the mixing takes place at from about 9° to about 25° C.

5. The method of claim 2 wherein the mixing takes place at from about 15° to about 17° C.

6. The method of claim 2 additionally including the step of homogenizing the stable emulsion.

7. The method of claim 2 wherein the cooling is to about 10° to about 11° C.

8. The method of claim 3 wherein the homogenizing is carried out in a colloid mill.

9. The method of claim 8 wherein the homogenizing is carried out in a colloid mill having about 7 to about 17 mil rotor/stator gap width, operating at about 1500 to about 1800 rpm at the rate of about 3.0 to about 4.5 liters/minute flow rate.

10. The method of claim 1 wherein the water-in-oil emulsion is a vehicle for an immunological substance.

11. The method of claim 1 wherein an antigen is incorporated in the aqueous phase prior to the addition of the aqueous phase to the oil.

12. The method of claim 11 wherein the antigen is influenza vaccine.

* * * * *